(12) United States Patent
Wagner et al.

(10) Patent No.: US 6,448,455 B1
(45) Date of Patent: Sep. 10, 2002

(54) TMP/VAPOR PRESSURE FILTRATION

(75) Inventors: Paul Wagner, Düsseldorf; Alexander Klausener, Pulheim, both of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/935,024

(22) Filed: Aug. 22, 2001

(30) Foreign Application Priority Data

Aug. 23, 2000 (DE) .......................................... 100 41 197

(51) Int. Cl.[7] .............................................. C07C 27/26
(52) U.S. Cl. ....................................... 568/854; 568/868
(58) Field of Search ................................. 568/854, 856, 568/868

(56) References Cited

U.S. PATENT DOCUMENTS

| | | | |
|---|---|---|---|
| 2,468,718 A | 4/1949 | Wyler | 260/635 |
| 4,514,578 A | 4/1985 | Immel et al. | 568/853 |
| 5,994,592 A | 11/1999 | Yokoyama et al. | 568/464 |
| 6,187,971 B1 | 2/2001 | Kratz et al. | 568/853 |

FOREIGN PATENT DOCUMENTS

DE  1 052 383  3/1959

OTHER PUBLICATIONS

Ullmann's Encyclopedia of Industrial Chemistry, 5th Edition, vol. A3 (month unavailable) 1985 p. 315, Azo Dyes.

Chemical Abstracts, vol. 70, No. 25, Jun. 23, 1969 Columbus, Ohio, US; abstract No. 0114517z, M.P. Vysotskii, et al.: "Removal of sodium formate and formic acid impurities from aqueous and nonaqueous solutions of the condensation products of aliphatic aldehydes and formaldehyde on ion–exchange resins" Seite 275; XP002184533 Zusammenfassung & Karbonilirovanie Nenasyshchennukh Uglevodorodov, 1968, Seiten 263–270.

R. Bott, et al.: "Dampf–Druckfiltration–die fortschrittliche Version der kontinuierlichen Druckfiltration (Hi–Bar Filtration)" Aufbereitungs–Technik, Bd. 37, Nr. 4, Apr. 1996 (1996–04), Seiten 163–170, XP000583092 Verlag für Aufbereiting Schirmer und Zeh, Wiesbaden, DE ISSN: 1443–9302 on der Anmeldung erwähnt das ganze Dokument.

*Primary Examiner*—Samuel Barts
*Assistant Examiner*—Elvis O. Price
(74) *Attorney, Agent, or Firm*—Joseph C. Gil; Richard E. L. Henderson; Diderico van Eyl

(57) ABSTRACT

The invention relates to a process for preparing trimethylolpropane with simultaneous formation of formate salts of the formula $$M(OOCH)_n \qquad (I),$$

where M represents the alkali metals lithium, sodium, potassium, rubidium, caesium and/or the alkaline earth metals beryllium, calcium, strontium, barium and n is 1 when M is an alkali metal and is 2 when M is an alkaline earth metal, where n-butyraldehyde, formaldehyde and a base are reacted by the inorganic Cannizzaro process and the reaction mixture formed is subjected to vapour pressure filtration as a suspension, if appropriate after partly removing distillable constituents, such as water.

13 Claims, No Drawings

TMP/VAPOR PRESSURE FILTRATION

BACKGROUND

The present invention relates to a process for preparing trimethylolpropane with simultaneous formation of a formate salt and to the separation of the formate salt from the reaction mixture, if appropriate, after prior concentration of this reaction mixture by evaporation.

Both trimethylolalkanes, and formate salts are products of industrial interest. Thus, trimethylolpropane is used in the production of surface coating resins, powder coatings, foams and a variety of polyesters. Formate salts can be utilized, for example, for producing formic acid. Calcium formate is particularly versatile and is used commercially in, for example, the following fields: additive in the field of animal nutrition (pig, cattle and turkey feed), use in the building materials industry (improving the curing of cement, gypsum plaster and jointing compositions and also as frost protection agent for mortar), auxiliary in the leather industry, auxiliary in the production of high-gloss papers, treatment of scrubbing water in flue gas de-sulphurization, auxiliary in silage production.

The industrial preparation of trimethylolpropane (TMP) is at present carried out by means of the inorganic Cannizzaro process, a process which simultaneously forms a formate salt. This process makes use of n-butyraldehyde and formaldehyde as starting materials. According to the generally accepted view, 2,2-dimethylolbutanal is initially formed in a base-catalysed aldol reaction via the intermediate 2-methylolbutanal. In the presence of stoichiometric amounts of a base, preferably sodium hydroxide or calcium hydroxide, across-Cannizzaro reaction occurs in the final step to form trimethylolpropane with simultaneous liberation of the corresponding formate salts. For example, calcium formate is formed when calcium hydroxide is used as base.

The formate salts formed have to be removed as completely as possible from the reaction mixture before the work-up by distillation to isolate the trimethylolpropane, since formate salts catalyse the of trimethylolpropane under distillation conditions. Furthermore, the formate salt has to be freed of organic residues and dried so as to be able to be used in a further application. Numerous methods of separating off the formate salt are known.

Thus, according to Ullmann's Encyclopaedia of Industrial Chemistry, 5th Edition 1985, p. 315, trimethylolpropane can be extracted by means of a suitable organic solvent from the reaction solution after the latter has been concentrated. The solvent is subsequently removed under reduced pressure and the crude trimethylolpropane obtained is purified by distillation. Alternatively, the aqueous reaction solution can be evaporated until the formate crystallizes. The mixture is subsequently filtered hot to remove the crystallized material.

DE-B 1 052 383 describes a process in which the trimethylolpropane is separated off by driving off the trimethylolpropane by means of superheated steam in a thin film evaporator. The process is advantageously carried out under reduced pressure and steam temperatures of from 120° C. to 220° C.

DE-A 32 07 746 describes a process for preparing trimethylolpropane using formaldehyde having a particularly low methanol content. To work up the reaction mixture, acid is added to it so as to give a pH of from 5 to 7. Excess formaldehyde is subsequently separated off by distillation. The trimethylolpropane is isolated by distillation or extraction.

The processes mentioned display technological difficulties in respect of the fractionation of reaction mixtures obtained in the preparation of trimethylolpropane by the Cannizzaro process. No optimal solution has yet been found for separating off the formates formed. This can also be seen from the fact that great efforts have been made in recent times to develop or to improve processes for the preparation of trimethylolpropane which proceed without formation of alkali metal formates or alkaline earth metal formates in the product mixture.

According to DE-A 1 952 738, the reaction of n-butyraldehyde and formaldehyde can be carried out in the presence of a lower tertiary amine. An approximately 6-fold excess of formaldyhyde and an approximately 1.5-fold excess of trialkylamine are used. Apart from the desired product trimethylolpropane, the process produces stoichiometric amounts of trialkylammonium formate which can easily be removed from the reaction mixture by distillation. However, unlike alkali metal formates or alkaline earth metal formates, this cannot be used further, so that it is proposed that the trialkylammonium formate be converted into calcium formate in a separate reaction step and the amine liberated in this step be returned to the circuit. This procedure makes the process economically unattractive.

According to DE-A 196 53 093, 2,2-dimethylolbutanal is firstly prepared by condensation of n-butyraldehyde and formaldehyde in the presence of catalytic amounts of a tertiary amine in three steps, with unreacted starting material and by-products formed being recycled and reacted further. The condensation product (2,2-dimethylolbutanal) obtained in this way is subsequently hydrogenated to give trimethylpropane. A usable formate is not obtained in this process.

EP-A 860 419, too, proposes carrying out the preparation of 2,2-dimethylolbutanal from n-butyraldehyde and formaldehyde in a plurality of stages, with the actual reaction occurring in the first stage and the 2-ethylacrolein obtained as by-product being reacted with further formaldehyde in the second stage. The 2,2-dimethylolbutanal prepared in this way can then be hydrogenated to give trimethylolpropane. Once again, no formate is isolated.

The known processes for preparing trimethylolpropane without formation of a formate salt have hitherto been inferior to the inorganic Cannizzaro process. This is firstly because formate salts are interesting and marketable products and secondly because a hydrogenation reaction can only be carried out in expensive equipment designed for this purpose.

It is an object of the present invention to provide a process for the simultaneous preparation of trimethylolpropane and a formate salt and for the effective isolation of both products, which process allows a high space-time yield and gives both products in very pure form. This object is achieved by means of the process of the invention.

SUMMARY

The invention relates to a process for preparing trimethylolpropane with simultaneous formation of formate salts of the formula (I):

$$M(OOCH)_n \qquad (I),$$

wherein M is a metal component selected from the group consisting of alkali metals (e.g., lithium, sodium, potassium, rubidium, caesium) and alkaline earth metals (e.g., beryllium, calcium, strontium, barium), and mixtures thereof, wherein n is 1 when M is an alkali metal and n is 2 when M is an alkaline earth metal. The process comprises reacting n-butyraldehyde and formaldehyde by an inorganic Cannizzaro process, forming a reaction mixture, and subjecting the reaction mixture formed to vapor pressure filtration. These and other features, aspects, and advantages of the present invention will become better understood with reference to the following description and appended claims.

DESCRIPTION

The invention provides a process for preparing trimethylolpropane with simultaneous formation of formate salts of the formula $$M(OOCH)_n \qquad (I),$$

where M represents the alkali metals lithium, sodium, potassium, rubidium, caesium and/or the alkaline earth metals beryllium, calcium, strontium, barium and n is 1 when M is an alkali metal and is 2 when M is an alkaline earth metal, characterized in that n-butyraldehyde, formaldehyde and a base are reacted by the inorganic Cannizzaro process and the reaction mixture formed is subjected to vapor pressure filtration.

Distillable constituents may optionally be partly removed in part from the reaction mixture prior to the vapor pressure filtration.

Further purification and drying steps can optionally be carried out after the vapour pressure filtration.

The process of the invention gives good space-time yields. As regards the formate isolated, degrees of purity and dryness which are not obtained by means of simple filtration, centrifugation or evaporative crystallization are achieved. The formate salts isolated are very substantially freed of adhering organic substances and of moisture without a plurality of process steps having to be carried out in succession in physically separate apparatuses.

The principles of the vapor pressure filtration method are described in DE-C 42 38 087 and in R. Bott, Th. Langeloh, Aufarbeitungstechnik 37, No. 4, 1996, 163-170. Fields of application mentioned are the filtration of coal slurries, pigment filtration, starch filtration, sugar filtration and hydrometallurgy. Thus, insoluble solids are always separated off from a suspension. Surprisingly, vapor pressure filtration can also be utilized for an extremely effective separation of formate salts in good quality from the mixtures formed in the course of the preparation and isolation of trimethylolpropane by the inorganic Cannizzaro process. This was not to be readily expected since in vapor pressure filtration, the filter cake formed is brought into contact with a gaseous treatment fluid, preferably steam and it was thus to be feared that appreciable amounts of the formate salt would be lost. However, residual formate salts in trimethylolpropane-containing filtrates have the disadvantages described above. In addition, it would have to have been feared that, in view of the comparatively high vapor temperatures, there would be adverse effects on the quality of the formate salt isolated due, for example, to thermal decomposition of organic components present in the mixture to be filtered.

In the process of the invention, n-butyraldehyde is firstly reacted with formaldehyde in the presence of a base. This reaction can be carried out in one or more stages. In the single-stage variant, the starting materials are reacted directly to form trimethylolpropane and a formate salt. In a two-stage variant, n-butyraldehyde and formaldehyde are firstly reacted in the presence of catalytic amounts of base to form 2,2-dimethylolbutanal, purification or separation steps are carried out if desired and only then is the 2,2-dimethylolbutanal reacted with further formaldehyde in the presence of stoichiometric amounts of base to form trimethylolpropane and formate salt.

The process of the invention produces, apart from trimethylolpropane, the formate salts of the formula $$M(OOCH)_n \qquad (I)$$

where M represents the alkali metals lithium, sodium, potassium, rubidium, caesium and/or the alkaline earth metals beryllium, calcium, strontium, barium and n is 1 when M is an alkali metal and is 2 when M is an alkaline earth metal.

M preferably represents sodium, potassium, rubidium, caesium, calcium, strontium and/or barium, particularly preferably sodium, potassium, caesium and/or calcium and very particularly preferably sodium and/or calcium.

Suitable bases are compounds selected from the group consisting of alkali metal hydroxides, alkaline earth metal hydroxides, alkali metal hydrogencarbonates and alkaline earth metal hydrogencarbonates and alkali metal carbonates and alkaline earth metal carbonates, with the base used naturally having to contain the alkali metal or alkaline earth metal ion which is to be present in the desired formate salt. Preferred bases are sodium hydroxide, calcium hydroxide, sodium hydrogencarbonate and sodium carbonate. The compounds can in each case be used alone or else as mixtures of two or more basic components of the substances mentioned. However, it is advisable to use only bases having an identical cation so as to obtain a uniform formate salt.

Formaldehyde is preferably used in the form of an aqueous solution which contains, for example, from about 5 to 99% by weight, preferably from 5 to 75% by weight, particularly preferably from 10 to 55% by weight, of formaldehyde. Formaldehyde is particularly preferably used in the form in which it is obtained in customary industrial processes for the preparation of formaldehyde.

The molar ratio of n-butyraldehyde to formaldehyde is, for example, from 1:2 to 1:10, preferably from 1:2 to 1:5, particularly preferably from 1:2 to 1:4.

The reaction can generally be carried out at a temperature of from 0 to 100° C., preferably from 10 to 90° C., particularly preferably from 15 to 70° C.

The residence time of the reaction mixture in the reactor can generally be from 0.15 to 10 hours.

The reaction can be carried out batchwise, in a semibatch mode or continuously. Possible reaction apparatuses are all reaction apparatuses known to those skilled in the art which are suitable for reaction of liquid reactants. Particular mention may be made of stirred tank reactors, cascades of stirred tanks, flow tubes and multichamber reactors.

The resulting product mixture comprising trimethylolpropane, formate salt and possibly further components such as water, alcohols, unreacted starting materials and by-products formed is, optionally after partial removal of distillable constituents, subjected, according to the invention, as a liquid/solid suspension to a vapor pressure filtration in which the formate salt is separated from the mixture, freed of organic impurities and demoisturized. This procedure can optionally be followed by further downstream purification and drying steps.

The above-mentioned partial removal of distillable constituents is preferably the partial removal of water by distillation and/or the partial or complete removal of further volatile components such as unreacted starting materials, relatively low-boiling by-products or small amounts of the trimethylolpropane product formed by distillation.

Suitable filtration apparatuses are described, for example, in DE-C 42 38 087. Such a filtration apparatus consists essentially of a filter area located in a housing, with the filter area being surrounded by a pressure-tight housing configured as a pressure chamber. The pressure chamber is filled with a gas under superatmospheric pressure. At least part of the filter area is surrounded by a hood which together with the filter area encloses a second pressure chamber containing the vapor treatment fluid in the gaseous state. The filtration apparatus contains washing devices for washing the filter cake, preferably tubes and nozzles, which may be located both under the hood and before or after it over the filter area.

According to the process of the invention, the formate salts can be separated off either continuously or batchwise. For continuous operation, it is possible to use, for example, drum, disc, belt or plate filters. For batchwise operation, suitable filters are, for example, suction filters. The separation is preferably carried out continuously using a rotating drum or disc filter, particularly preferably using a rotating drum filter.

The mixture to be filtered which is fed to the vapor pressure filtration generally contains, for example, from 5 to 95% by weight, preferably from 6 to 90% by weight, particularly preferably from 7 to 85% by weight and very particularly preferably from 8 to 75% by weight, of trimethylolpropane. It additionally contains, for example, from 5 to 95% by weight, preferably from 6 to 90% by weight, particularly preferably from 7 to 85% by weight and very particularly preferably from 8 to 75% by weight, of the formate salt and from 5 to 95% by weight, preferably from 6 to 90% by weight, particularly preferably from 7 to 85% by weight and very particularly preferably from 8 to 80% by weight, of water. In addition, further components such as unreacted starting materials or organic impurities may be present.

The temperature of the mixture fed to the vapor pressure filtration can be, for example, from 0° C. to 150° C., preferably from 5° C. to 120° C. and particularly preferably from 10° C. to 110° C.

In vapor pressure filtration, 4 phases, namely cake formation, cake washing, vapor treatment of the cake and demoisturization of the cake, are generally carried out. Cake washing can be carried out before, during and/or after vapor treatment of the cake. However, it is also possible to carry out vapor pressure filtration without cake washing, since the vapor treatment of the cake likewise effects washing. Preference is given to carrying out the phase of cake washing.

The reaction mixture obtained in the preparation of trimethylolpropane by the inorganic Cannizzaro process is, optionally after preliminary partial evaporation to separate off low-boiling impurities, for example unreacted formaldehyde and part of the water present in the reaction mixture, fed to the vapor pressure filtration apparatus. A filter cake of the formate salt is formed on the filter area.

During the cake formation phase, it is advantageous to apply a differential pressure. This is, for example, in the range from 0 to 6 bar, preferably from 0.3 to 4 bar particularly preferably from 0.5 to 3 bar.

The cake formation phase generally lasts for from 2 to 420 seconds, preferably from 3 to 360 seconds and particularly preferably from 4 to 300 seconds.

Filter media which can be used are, for example, woven metal meshes or heat-resistant polymer materials.

Cake formation can be followed by cake washing and vapor treatment of the cake in any order; cake washing is preferably carried out first.

Cake washing can consist of one or more washing steps. For this purpose, the filter cake is treated with one or more identical or different washing liquids. For washing a formate salt cake obtained according to the invention, the following washing liquids have been found to be particularly useful: pure water and/or steam or its condensate, and/or the water containing the formate salt to be isolated, preferably water partially saturated, saturated or supersaturated with the formate salt to be isolated and/or a filtrate obtained in the vapor pressure filtration, with the washing liquids being able to be used in pure form or as mixtures of any of them.

The filtrates from different regions of the filter are advantageously discharged separately and collected separately. The filtrates can then be directed to specific further processing. To optimize washing, it is advantageous, as mentioned above, to return one or more of these filtrates to the vapor pressure filtration as washing liquid.

The temperatures of the washing liquids are, for example, in the range from 0° C. to 165° C., preferably from 5° C. to 155° C. and particularly preferably from 10° C. to 145° C.

The differential pressure across the filter cake during cake washing is, for example, from 0 to 6 bar, preferably from 0.3 to 4 bar, particularly preferably from 0.5 to 3 bar.

The cake washing phase lasts, for example, for from 0 to 420 seconds, preferably from 1 to 360 seconds and particularly preferably from 2 to 300 seconds.

In the vapor treatment of the cake, the filter cake of formate salt formed on the filter area is treated with a gaseous treatment fluid whose pressure and temperature are set so that the treatment fluid condenses in the filter cake, preferably initially in the uppermost layer of the filter cake farthest from the filter area, so that a condensation front is formed along this layer and that, in addition, the filter cake is heated to the temperature of the gaseous treatment fluid progressively from the uppermost layer in the direction of the filter area, so that the condensation front at the phase boundary between the gaseous treatment fluid and the liquid is shifted towards the filter area. The gaseous phase of the treatment fluid can be used as pressure medium for generating a differential pressure. The cake can once again be washed, heated and mechanically and thermally demoisturized by means of the vapor treatment of the cake.

As treatment fluid, preference is given to using deionized water. However, it is also possible to use other treatment fluids, for example organic solvents.

The temperature of the vapor which is fed to the vapor pressure filtration can be, for example, from 100° C. to 250° C., preferably from 105° C. to 220° C. and particularly preferably from 110° C. to 200° C.

The differential pressure across the filter cake during the vapor treatment of the cake is, for example, in the range from 0 to 6 bar, preferably from 0.3 to 4 bar, particularly preferably from 0.5 to 3 bar.

The vapor treatment of the cake lasts, for example, for from 0.5 to 300 seconds, preferably from 0.5 to 240 seconds and particularly preferably from 0.5 to 180 seconds.

Cake washing and vapor treatment of the cake can be followed by demoisturization of the cake. Here, the filter cake is, for example, demoisturized mechanically and thermally by means of superheated steam, by means of compressed inert gas and/or compressed air. Air which has been compressed and optionally heated is preferably used for demoisturizing the formate salt cake.

The differential pressure in the cake demoisturization phase is, for example, in the range from 0 to 6 bar, preferably from 0.3 to 4 bar, particularly preferably from 0.5 to 3 bar.

The temperature of the compressed inert gas or the compressed air is, for example, in the range from 0° C. to 250° C., preferably from 10° C. to 220° C. and particularly preferably from 20° C. to 200° C.

The cake demoisturization phase lasts, for example, for from 0 to 300 seconds, preferably from 0.5 to 260 seconds and particularly preferably from 0.5 to 180 seconds.

The washed, vapor-treated and demoisturized formate filter cake can be taken from the filter cloth and conveyed out of the pressure chamber via a cake discharge lock.

The formate salt obtained in this way generally has a residual moisture content of 0.1–3.5% by weight, preferably 0.1–3.0% by weight. The content of organic impurities is, for example, <500 ppm, preferably <300 ppm.

In contrast to the methods known hitherto for working up mixtures containing trimethylolpropane and a formate salt, vapor pressure filtration allows not only the separation of the formate salt from the mixtures obtained in the course of the preparation and isolation of trimethylolpropane but also the removal of adhering organic residues and the demoisturization of the formate salt. This leads to a further improvement in the purity of the formate salt.

The trimethylolpropane-containing filtrates obtained in the vapor pressure filtration are largely free of formate salts, so that trimethylolpropane can be isolated in a manner known per se. The filtrates are generally worked up by distillation.

The vapor condensate obtained and the washing filtrates can, optionally after prior work-up, be passed to regulated disposal. However, it may be more economically advantageous to return some or all of these, continuously or discontinuously, to a suitable point in the process, for example, as washing liquids.

The formate salt obtained can be used further in the form as discharged, but it is also possible, if desired, for it to be passed to one or more further isolated or combined purification and drying steps. For this purpose, all known purification and drying processes suitable for the present case can be employed. Examples of purification processes are: recrystallization from water or a water-containing solvent mixture or redispersion in water or a water-containing solvent mixture. Examples of drying processes are: convection drying (circulated air drying, belt drying, fluidized-bed drying, stream drying or atomization drying), contact drying (plate dryers, double cone dryers, blade dryers), freeze drying or radiation drying.

The following example illustrates the process of the invention without implying any restriction of the scope of the invention, in which all parts and percentages are by weight unless otherwise indicated.

EXAMPLE 240 g of a mixture containing about 45% by weight of trimethylolpropane, about 28% by weight of calcium formate, about 20% of water and further organic components was fed to a laboratory pressure filter cell having a filter area of 22 cm$^2$ (filter material: polypropylene filter cloth, 25 μm). A pressure of 2 bar was applied by means of compressed air to the mixture to be filtered; the pressure on the filtrate side was about 1 bar. The cake formation time was 26 seconds. The filter cake was subsequently washed on the filter for 25 seconds using 80 g of a saturated aqueous solution of calcium formate. The filter cake was then treated for 9.3 seconds with steam which had been depressurized to 2 bar. The hot filter cake was subsequently dried for 26 seconds by means of compressed air.

This gave 65 g of calcium formate which had a residual moisture content of 1.95% by weight (K. Fischer) and a residual organics content of 77 mg/kg.

Although the present invention has been described in detail with reference to certain preferred versions thereof, other variations are possible. Therefore, the spirit and scope of the appended claims should not be limited to the description of the versions contained therein.

What is claimed is:

1. A process for preparing trimethylolpropane with simultaneous formation of formate salts of the formula (I):

$$M(OOCH)_n \qquad (I),$$

wherein M is a metal selected from the group consisting of alkali metals, alkaline earth metals, and mixtures thereof, wherein n is 1 when M is an alkali metal and n is 2 when M is an alkaline earth metal, the process comprising reacting n-butyraldehyde and formaldehyde by an inorganic Cannizzaro process, forming a reaction mixture, and subjecting the reaction mixture formed to vapor pressure filtration.

2. The process according to claim 1, wherein M represents sodium or calcium.

3. The process according to claim 1, wherein formate salt is isolated and has a residual moisture content of <3.5% by weight.

4. The process according to claim 1, wherein the vapor pressure filtration is carried out continuously.

5. The process according to claim 1, wherein the differential pressure in the vapor pressure filtration is from 0 to 6 bar.

6. The process according to claim 1, wherein a filter cake is formed in the vapor pressure filtration and the filter cake is subjected to at least one washing step during the filtration procedure.

7. The process according to claim 6, wherein the washing of the cake is carried out using a fully saturated or partially saturated aqueous solution of the formate salt to be isolated.

8. The process according to claim 7, wherein distillable constituents are partly separated from the resulting reaction mixture prior to the formate salt being separated off.

9. The process according to claim 6, wherein cake formation, cake washing, vapor treatment of the cake and demoisterizataion of the cake are carried out during the vapor pressure filtration.

10. The process according to claim 9, wherein in the vapor treatment of the cake, the filter cake of formate salt to be separated off formed on the filter area is treated with a gaseous treatment fluid whose pressure and temperature are set so that the treatment fluid condenses in the filter cake, optionally initially in the uppermost layer of the filter cake farthest from the filter area, so that a condensation front is formed along this layer and that, in addition, the filter cake is heated to the temperature of the gaseous treatment fluid progressively from the uppermost layer in the direction of the filter area, so that the condensation front at the phase boundary between the gaseous treatment fluid and the liquid is shifted towards the filter area.

11. The process according to claim 9, wherein in the demoisturization of the cake, the filter cake of formate salt to be separated off formed on the filter area is treated with compressed inert gas and/or compressed air.

12. The process according to claim 1, wherein the reaction mixture after the vapor pressure filtration is subjected to at least one further purification and drying step which comprises a recrystallization from and redispersion in a solvent, or redispersion in a solvent.

13. The process according to claim 12, wherein the solvent is water or a water-containing mixture.

* * * * *